United States Patent [19]
Kadkhodayan et al.

[11] Patent Number: 5,380,448
[45] Date of Patent: Jan. 10, 1995

[54] PROCESS FOR METAL SALTS OF HYDROCARBYL DITHIOPHOSPHORIC ACID

[75] Inventors: Abbas Kadkhodayan, Collinsville, Ill.; Dale G. Pillsbury, Oilville, Va.; Paul G. Griffin, Collinsville, Ill.

[73] Assignee: Ethyl Petroleum Additives, Inc., Richmond, Va.

[21] Appl. No.: 192,369

[22] Filed: Feb. 7, 1994

[51] Int. Cl.$^6$ .............................. C10M 1/48
[52] U.S. Cl. .................. 252/32.7 E; 252/18; 252/35; 252/49.9; 556/25
[58] Field of Search ........... 252/32.7 E, 18, 49.9, 252/32.7 R, 35; 556/25

[56] References Cited

U.S. PATENT DOCUMENTS

| | | | |
|---|---|---|---|
| 2,838,555 | 6/1958 | Goldsmith | 260/429.9 |
| 3,086,939 | 4/1963 | Tichelaar et al. | 252/18 |
| 3,234,250 | 2/1966 | Schneider et al. | 556/25 |
| 3,361,667 | 1/1968 | Wenborne et al. | 252/32.7 |
| 3,489,682 | 1/1970 | Lesuer | 252/32.7 |
| 4,085,053 | 4/1978 | Caspari | 252/32.7 E |
| 4,123,370 | 10/1978 | Meinhardt | 252/32.7 E |
| 4,215,067 | 7/1980 | Brannen et al. | 260/429.9 |
| 4,263,150 | 4/1981 | Clason et al. | 252/32.7 E |
| 4,634,541 | 1/1987 | Caspari et al. | 252/32.7 E |
| 5,015,402 | 5/1991 | Yodice et al. | 252/32.7 E |

FOREIGN PATENT DOCUMENTS

| | | |
|---|---|---|
| 2417388 | 1/1984 | Germany . |
| 968801 | 9/1964 | United Kingdom . |
| 9303121 | 2/1993 | WIPO . |

*Primary Examiner*—Prince Willis, Jr.
*Assistant Examiner*—Cephia D. Toomer

[57] ABSTRACT

This invention relates to a process for preparing an overbased metal salt of hydrocarbyl dithiophosphoric acid comprising neutralizing hydrocarbyl dithiophosphoric acid with an amount of metal oxide sufficient to form said overbased metal salt of hydrocarbyl dithiophosphoric acid, which metal oxide has a surface area of no less than about 4 $m^2$ per gram up to about 12 $m^2$ per gram and whereby the overbased metal salt of hydrocarbyl dithiophosphoric acid thus formed has a base metal to phosphorus weight ratio within the range of greater than about 1.2:1 up to about 1.3:1.

15 Claims, No Drawings

PROCESS FOR METAL SALTS OF HYDROCARBYL DITHIOPHOSPHORIC ACID

BACKGROUND

This invention relates to a process for the production of metal salts of hydrocarbyl dithiophosphoric acid particularly, overbased metal salts of hydrocarbyl dithiophosphoric acid.

It is well known that various additives can be used in lubricating oils in order to improve certain oil properties and to make a more satisfactory lubricant. For example, antiwear agents are intended to decrease wear of machine parts. Wear inhibitors for incorporation in motor oils and industrial oils are finding greater use as a result of greater stress placed on moving parts in high performance engines. Numerous other additives have been developed for use in such oil compositions to improve the lubricating characteristics thereof and thereby to lessen the wear of the moving parts.

Of the antiwear agents, the metal salts of hydrocarbyl dithiophosphoric acid, such as the diaryl and dialkyl dithiophosphates, especially zinc dithiophosphates, have long been used as antiwear additives and antioxidants in hydraulic oils, motor oils, automatic transmission fluids and the like. Processes for the production of metal salts of hydrocarbyl dithiophosphoric acid are well known. See U.S. Pat. Nos. 2,838,555; 3,848,032; 4,085,053; 4,123,370; 4,215,067; and 4,263,150 incorporated herein by reference. In a typical reaction, four equivalents of a hydroxy compound are reacted with phosphorus pentasulfide in the presence of a catalyst. Once formed, the hydrocarbyl dithiophosphoric acid is then separated from the reaction mass, and subsequently neutralized with an excess of metal base such as zinc oxide.

An important characteristic in determining the antiwear properties of the overbased metal salt of hydrocarbyl dithiophosphoric acid is the metal to phosphorus ratio. Typically, the metal to phosphorus ratio should be no less than about 1.15:1 and most preferably greater than about 1.2:1. However, variations in reactants and process conditions result in undesirable variations in the metal to phosphorus ratios of the products thus formed. If the metal salt of dithiophosphoric acid has too low a metal to phosphorus ratio, blending of the reaction product with a product having a higher metal to phosphorus ratio is required. It is desirable therefore to provide a process which will more consistently result in a clear reaction product having a metal to phosphorus ratio of no less than about 1.15:1.

THE INVENTION

A process has now been discovered which can be used to more consistently provide metal salts of hydrocarbyl dithiophosphoric acid having high metal to phosphorus ratios, e.g., metal to phosphorus ratios of no less than about 1.15:1. The process comprises neutralizing hydrocarbyl dithiophosphoric acid with an amount of metal oxide sufficient to form said overbased metal salt of hydrocarbyl dithiophosphoric acid, which metal oxide has a surface area of no less than about 4 $m^2$ per gram up to about 12 $m^2$ per gram and whereby the overbased metal salt of hydrocarbyl dithiophosphoric acid thus formed has a base metal to phosphorus weight ratio within the range of greater than about 1.2:1 up to about 1.3:1.

While it is known to use metal oxides to prepare metal salts of hydrocarbyl dithiophosphoric acid, it has been found, quite surprisingly and unexpectedly, that the surface area of the metal oxide is a critical characteristic of the metal oxide which effects the ratio of the base metal to phosphorus of the overbased metal salt of the hydrocarbyl dithiophosphoric acid reaction product. Typically, the higher the surface area of the metal oxide, the higher will be the metal to phosphorus ratio of the finished overbased product.

In another embodiment, this invention provides a process for preparing an overbased metal salt of hydrocarbyl dithiophosphoric acid comprising:

a) forming a reaction mixture containing (i) basic metal salt of hydrocarbyl dithiophosphoric acid, and (ii) metal oxide wherein the weight ratio of (i) to (ii) is within the range of from about 0.5:1 to about 4:1;

b) feeding to the reaction mixture in (a) hydrocarbyl dithiophosphoric acid thereby forming a reaction mass;

c) subsequent to step (b) feeding from about 1 to about 8 moles of water per mole of metal oxide to the reaction mass; and d) reacting the reaction mass in (c) at a temperature and for a period of time, which time and temperature are sufficient to form basic metal salt of dihydrocarbyl dithiophosphoric acid having a base metal to phosphorus weight ratio within the range of greater than about 1.2:1 up to about 1.3:1.

It has also been discovered, quite surprisingly, that the use of an amount of basic metal salt of hydrocarbyl dithiophosphoric acid to slurry the metal oxide prior to the neutralization reaction and addition of water to the reaction mass provides an increase in the metal to phosphorus ratio of the finished overbased product. The basic metal salt of hydrocarbyl dithiophosphoric acid may be prepared initially utilizing water or process oil to slurry the metal oxide. After an initial neutralization reaction, a reaction heel from a previous reaction containing the basic metal salt product may be used to slurry the metal oxide. While the reaction heel may contain metal oxide solids and other impurities in addition to the basic metal salt of hydrocarbyl dithiophosphoric acid, for the purposes of this invention, the reaction heel need not be filtered prior to use for slurrying the metal oxide in a subsequent neutralization reaction.

The amount of basic metal salt of hydrocarbyl dithiophosphoric acid used to slurry the metal oxide is not critical to the invention, but will normally be within the range of from about 0.5 to about 5 parts by weight of metal salt per part of metal oxide, preferably from about 0.8 to about 3 parts by weight of metal salt per part of metal oxide, and most preferably, from about 1 to about 2 parts by weight per part of metal oxide.

The method for preparing the hydrocarbyl dithiophosphoric acid for reaction with a metal oxide is also not critical to the invention and, thus, any of the well known processes for the thioacid formation reaction may be used. Generally, one mole of phosphorus pentasulfide ($P_2S_5$) is reacted in an agitated vessel with about four equivalents of alcohol in the presence of a nitrogen containing catalyst at a temperature within the range of from about 40° to about 120° C., most preferably about 100° to about 110° C. for alkyl alcohols having a boiling point higher than about 100° C. It is preferred to have an excess of alcohol present in the reaction mass, most preferably an excess of about 15 mole percent alcohol based on the number of moles of phosphorus sulfide reactant. Excess phosphorus sulfide in the reaction mass is generally avoided since when there is an excess of $P_2S_5$ in the reaction mass, there is a tendency to form excess quantities of hydrogen sulfide gas which must be removed and disposed of prior to the neutralization step.

The phosphorus sulfide reactant used in the thioacid formation step of this invention may be selected from any one or more of $P_2S_3$, $P_2S_5$, $P_4S_7$, $P_4S_3$, $P_4S_9$, or mixtures of the foregoing with phosphorus pentasulfide being the most preferred. Such phosphorus sulfide compositions may contain minor amounts of free sulfur. While the structure of phosphorus pentasulfide is generally represented as $P_2S_5$, the actual structure is believed to contain four phosphorus atoms and ten sulfur atoms, i.e., $P_4S_{10}$. Accordingly, one mole of $P_4S_{10}$ will react with eight equivalents of hydroxy compound to produce the thioacid. For the purposes of this invention, the phosphorus sulfide reactant will be considered as a compound having the structure of $P_2S_5$ with the understanding that the actual structure is probably $P_4S_{10}$.

The hydroxy compounds from which the hydrocarbyl dithiophosphoric acids are derived can be represented generically by the formula ROH wherein R is hydrocarbyl or substituted hydrocarbyl group. Mixtures of hydroxy compounds may also be used. As is recognized in the art, these hydroxy compounds need not be monohydroxy compounds. That is, the hydrocarbyl dithiophosphoric acids may be prepared from mono-, di-, tri-, tetra-, and other polyhydroxy compounds, or mixtures of two or more of the foregoing.

Examples of the general class of compounds corresponding to the formula ROH are those wherein R is selected from an alkyl, cycloalkyl, alkyl-substituted cycloalkyl, aryl, alkaryl, arylalkyl, alkoxyalkyl, alkoxyaryl, haloalkyl, haloaryl, nitroaryl radical, and the like. Specific examples of such hydroxy compounds are phenol, resorcinol, hydroquinone, catechol, cresol, xylenol, hydroxydiphenyl, benzylphenol, phenylethylphenol, methyl-hydroxydiphenyl, guaiacol, alpha- and beta-naphthol, alpha- and beta-methylnaphthol, tolylnaphthol, benzylnaphthol, anthranol, phenylmethylnaphthol, phenanthrol, monomethyl ether of catechol, anisole, chlorophenol, octyl alcohol, cyclohexanol, 2-ethylhexanol, isopropanol, methylcyclo-hexanol, cycloheptanol, cyclopentanol, 2,4-diamylphenoxy-phenol, butanol, isoamyl alcohol, oleyl alcohol, dodecanol, lauryl alcohol, cetyl alcohol, ethylene glycol, propylene glycol, octylphenoxy-ethanol, methanol, ethyl alcohol, neopentyl alcohol, isohexyl alcohol, 2,3-dimethylbutanol-1, n-heptanol, diisopropyl carbinol, glycerol, diethylene glycol, capryl alcohol, nonylphenol, decylphenol, and the like. Of the foregoing, the aliphatic alcohols and branched aliphatic alcohol are preferred. More preferred are the aliphatic alcohols having from 3 to 40 carbon atoms, most preferably 2-ethylhexanol. It is to be understood that most commercially available alcohols are not pure compounds but are mixtures containing a predominant amount of the desired alcohol and minor amounts of various isomers and/or longer or shorter chain alcohols.

The dithiophosphoric acid formation reaction is typically conducted under substantially anhydrous conditions, in the absence of solvent, and in the presence of a catalytic amount of nitrogen containing catalyst. The nitrogen containing catalyst may be selected from $NH_3$ or a compound characterized by the presence within its structure of at least one group of the formula

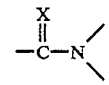

wherein X is oxygen or a divalent sulfur atom. By "catalytic amount of catalyst" means that amount of catalyst which will provide the desired results in a given reaction for preparing a hydrocarbyl dithiophosphoric acid. Based on the total weight of $P_2S_5$ reactant used, the amount of catalyst will generally be within the range of from about 0.005% to about 1% by weight of $P_2S_5$ reactant. Illustrative nitrogen containing compounds containing the structure of the above formula include N-vinyl pyrrolidone, pyrrolidone, caprolactam, urea, thiourea, acetamide, benzamide, N,N-dimethylformamide, oleamide, linoleamide, or mixtures of two or more of the foregoing. The 5-, 6-, and 7-membered lactams are preferred catalysts with caprolactam being especially preferred.

Once the hydrocarbyl dithiophosphoric acid reaction is complete, the hydrocarbyl dithiophosphoric acid product may be stripped and cooled with an inert gas such as nitrogen to remove all traces of hydrogen sulfide. Any unreacted alcohol, $P_2S_5$ or other solids can be removed by decantation, filtration, or centrifugation.

The hydrocarbyl dithiophosphoric acid can be neutralized and overbased by contacting a slurry containing metal oxide with the hydrocarbyl dithiophosphoric acid. Such a slurry may be formed initially from water and metal oxide, and after the first neutralization reaction, is preferably formed by mixing metal oxide with basic metal salt of hydrocarbyl dithiophosphoric acid. The amount of metal oxide used in the neutralization step is that amount sufficient to form the overbased metal salt of hydrocarbyl dithiophosphoric acid having a metal to phosphorus ratio of about 1.15:1 or higher. Typically an excess of metal oxide is used, preferably a molar excess of from about 10 to about 50%, more preferably, 15 to about 40%, and most preferably about 25 to 30%. When water is used to slurry the metal oxide, the amount of water is generally within the range of from about 2 to 10 moles of water per mole of metal oxide. In a particularly preferred embodiment, the slurry is formed by combining metal oxide with a heel from a previous neutralization reaction wherein the heel contains basic metal salt of hydrocarbyl dithiophosphoric acid.

Alternatively, the hydrocarbyl dithiophosphoric acid may be neutralized in the presence of a catalytic amount of alkali or alkaline earth metal hydroxide, oxide, halide, or carbonate, or a mixture thereof provided that the metal of the catalyst is not the same metal as the metal of the metal oxide reactant. When used, the catalyst is preferably calcium, potassium, or sodium hydroxide, most preferably sodium hydroxide. A typical amount of catalyst ranges from about 0.001 to about 0.05 equivalents of alkali or alkaline earth metal per equivalent of phosphorus in the acid or its salt.

Subsequent to the formation of the metal oxide slurry, the slurry is heated to a temperature above about 40° C. up to about 130° C., preferably above about 50° C., most preferably within the range of from about 55° to about 75° C. Upon reaching the desired temperature, hydrocarbyl dithiophosphoric acid is then charged to the metal oxide slurry in the reaction vessel. During the thioacid addition, the reaction mass is typically controlled at a temperature within the range of from about 70° to about 90° C. The rate of thioacid addition to the reaction mass is not critical to the invention and may range from 5 minutes to 10 hours or more. In general, depending on the reaction mass size and scale of reaction, the thioacid addition can generally be completed within about 1 hour.

When utilizing a reaction heel to slurry the metal oxide, water is added to the reaction mass upon completion of the thioacid addition and neutralization of the thioacid so as to hydrolyze a sufficient amount of metal oxide to obtain the desired overbased product having a total base number (TBN) within the range of from about 5 to about 40. Subsequent to the water addition, the reaction mass is cooked for a period of time sufficient to assure substantially complete neutralization and overbasing of the metal salt of thioacid. The cook period may extend from about 10 minutes to about 10 hours or more, again depending upon the mechanical equipment size and scale of reaction. After the cook period, the product is dehydrated, typically under subatmospheric pressure and filtered to obtain the basic metal salt of hydrocarbyl dithiophosphoric acid.

In order to maintain the desired temperature during neutralization, the reaction vessel may be subjected to subatmospheric pressures when water is used to slurry the zinc oxide, whereby a portion of the water provides evaporative cooling of the reaction mass. Suitable subatmospheric pressures can be determined by simple trial and error techniques and will vary with mechanical configuration and reaction mass size. Typically, a subatmospheric pressure of about 250 mm of Hg is sufficient to maintain the desired reaction mass temperature in a 1 liter reaction vessel. In commercial scale reactions, suitable temperature control may be obtained utilizing internal or external cooling of the reaction vessel contents by the use of cooling coils, reactor cooling jackets, heat exchange circulation loops, and the like as well as by water evaporation techniques. When mechanical cooling means alone are used to cool the reactor contents, the reaction may be suitably conducted under atmospheric, subatmospheric, or superatmospheric pressures.

When a reaction heel is used to slurry the metal oxide instead of water, the neutralization reaction may likewise be conducted under atmospheric, subatmospheric, or superatmospheric pressures. Since water is added after the thioacid addition to the reaction mass is complete, the reaction mass temperature typically does not tend to rise as rapidly during neutralization. Hence, the reaction mass temperature may be suitably controlled by mechanical means alone rather than by evaporative techniques.

The basic metal salts of hydrocarbyl dithiophosphoric acid formed in the neutralization step include the aluminum, tin, cobalt, lead, molybdenum, zinc, barium, calcium, strontium, chromium, iron, cadmium, magnesium, or nickel salts of hydrocarbyl dithiophosphoric acid made by neutralization of hydrocarbyl dithiophosphoric acid with aluminum, tin, cobalt, lead, molybdenum, zinc, barium, calcium, strontium, chromium, iron, cadmium, magnesium or nickel base. Of the basic metals, zinc oxide is preferred with high surface area zinc oxide being the most preferred. By "high surface area" means that the zinc oxide has a surface area of greater than about 3 m² per gram, preferably from about 5 to about 10 m² per gram.

In order to further illustrate the advantages of this invention, the following illustrative examples are given.

EXAMPLE 1

Preparation of di-2-ethylhexyl-dithiophosphoric acid

Into a 1 liter, 3-neck stirred glass reactor having a thermometer and temperature controlled heating mantle and H$_2$S exhaust means were placed 0.2 grams (1.77 mmols) of caprolactam and 135.1 grams (1.04 mols) of 2-ethylhexanol. Phosphorus pentasulfide, 222.3 grams (1.0 mol) was transferred into a dry 500 mL round bottom flask. The reactor contents were heated to 65° C. and the phosphorus pentasulfide was added over a one hour period into the reactor using a collapsible rubber tube connection. The temperature of the reactor contents was allowed to rise to 75°–80° C. during the phosphorus pentasulfide addition. At the end of the phosphorus pentasulfide addition, 405.4 grams (3.1 mols) of 2-ethylhexanol was added to the reactor over a 2.5 hour period using an addition funnel while maintaining the temperature between 84°–88° C. Subsequent to the alcohol addition, the reaction mass was cooked for 1.5 hours at 84°–88° C. The entire reaction was conducted under a nitrogen pressure in order to prevent the escape of H$_2$S. Upon completion of the cook period, the reaction mass was filtered and the di-2-ethylhexyl-dithiophosphoric acid was collected.

EXAMPLE 2

Preparation of overbased zinc di-2-ethylhexyldithiophosphate

Standard Procedure

Into a 1-liter glass reaction vessel equipped with a baffle, a four blade 45° pitch agitator, a thermometer and a heating mantle was charged 108 grams (6 mols) of water. The reactor contents were heated to 65° C. and the agitator was set at 700 rpm. Once the agitation rate was set, zinc oxide (55.3 grams, 0.68 mols) was charged to the reactor. Next 400 grams (1.13 mols) of di-2-ethylhexyl-dithiophosphoric acid from Example 1 was charged to a 500 mL pressure equalizing graduated funnel which was connected to the reactor using a glass offset adaptor. Vacuum was applied to the reactor vessel at 254 mm of Hg. When the temperature of the reactor contents obtained 65° C., the thioacid addition was begun and the temperature controller for the heating mantle was set at 75°–80° C. The thioacid was added to the reaction vessel over a 1 hour time period while maintaining the preset temperature and vacuum of 254 mm Hg. Once all of the acid was charged, the reactor contents were cooked for 1 hour at 75°–80° C. and 254 mm Hg vacuum. At the end of the cook period, the temperature controller was set at 85°–90° C. and the vacuum was raised to between 430 and 530 mm Hg so as to attain a dehydration rate of approximately 1 mL of distillate per minute and to maintain a temperature between 75°–79° C. The vacuum and dehydration temperatures were maintained for about 3 hours while monitoring the temperature of the reactor contents. At the end of the dehydration step, as indicated by a sharp rise in the reactor contents temperature, the vacuum was increased to 711 mm Hg and the temperature increased to 85°–90° C. for a one hour final cook period. After the final cook period, the product was filtered using 2.5 grams of filter aid, #2 qualitative 5.5-cm filter paper, and a vacuum filter funnel.

EXAMPLE 3

Preparation of overbased zinc di-2-ethylhexyldithiophosphate

Reaction Heel Procedure

Into a 1-liter glass reaction vessel equipped with a baffle, a four blade 45° pitch agitator, a thermometer and a heating mantle was charged 80 grams of crude heel (unfiltered overbased zinc di-2-ethylhexyldithiophosphate from a previous reaction) and 55.3 grams (0.68 mols) of zinc oxide. The reactor contents were heated to 65° C. and the agitator was set at 700 rpm. Once the agitation rate was set, 400 grams (1.13 mols) of di-2-ethylhexyl-dithiophosphoric acid from Example 1 was charged to a 500 mL pressure equalizing graduated funnel which was connected to the reactor using a glass offset adaptor. When the temperature of the reactor contents obtained 65° C., the thioacid addition was begun and the temperature controller for the heating mantle was set at 75°-80° C. The thioacid was added to the reaction vessel over a 1 hour time period while maintaining the preset temperature. Ten minutes after the thioacid addition was completed, 72 grams (4 mols) of water was added to the reaction vessel all at once. The reactor contents were then cooked for 50 minutes at 75°-80° C. At the end of the cook period, the temperature controller was set at 85°-90° C. and the pressure in the reaction vessel was lowered to between 430 and 530 mm Hg so as to attain a dehydration rate of approximately 1 mL of distillate per minute and to maintain a temperature between 75°-80° C. The vacuum and dehydration temperatures were maintained for about 1 hour while monitoring the temperature of the reactor contents. At the end of the dehydration step, as indicated by a sharp rise in the reactor contents temperature, the vacuum was increased to 711 mm Hg and the temperature increased to 85°-90° C. for a one hour final cook period. After the final cook period, the product was filtered using 2.5 grams of filter aid, #2 qualitative 5.5-cm filter paper, and a vacuum filter funnel.

In the following Tables 1–4, a different thioacid batch was used for each set of runs comparing the Example 2 procedure with the Example 3 procedure.

TABLE 1

| Ex. No. | Zn (wt. %) | P (wt. %) | Zn/P ratio | S (wt. %) | Visc 40° C. (cSt) | TBN (mg KOH/g) | pH |
|---|---|---|---|---|---|---|---|
| 2 | 9.47 | 7.86 | 1.20 | 15.1 | 337 | 12.6 | 6.6 |
| 3 | 9.80 | 7.81 | 1.26 | 15.1 | 417 | 18.7 | 6.8 |

TABLE 2

| Ex. No. | Zn (wt. %) | P (wt. %) | Zn/P ratio | S (wt. %) | Visc 40° C. (cSt) | TBN (mg KOH/g) | pH |
|---|---|---|---|---|---|---|---|
| 2 | 9.28 | 7.85 | 1.18 | 15.2 | 298 | 7.3 | 6.6 |
| 3 | 9.64 | 7.80 | 1.24 | 15.2 | 355 | 12.8 | 6.8 |

TABLE 3

| Ex. No. | Zn (wt. %) | P (wt. %) | Zn/P ratio | S (wt. %) | Visc 40° C. (cSt) | TBN (mg KOH/g) | pH |
|---|---|---|---|---|---|---|---|
| 2 | 9.26 | 7.89 | 1.17 | 15.0 | 290 | 6.3 | 6. |
| 3 | 9.45 | 7.80 | 1.21 | 14.9 | 348 | 12.8 | 6.7 |

TABLE 4

| Ex. No. | Zn (wt. %) | P (wt. %) | Zn/P ratio | S (wt. %) | Visc 40° C. (cSt) | TBN (mg KOH/g) | pH |
|---|---|---|---|---|---|---|---|
| 2 | 9.25 | 7.87 | 1.16 | 15.0 | 302 | 6.2 | 6.4 |
| 3 | 9.49 | 7-9 | 1.20 | 15.0 | 350 | 13.7 | 6.7 |

As can be seen from the foregoing examples, there is a significant increase in the zinc to phosphorus ratio for metal salt products of dithiophosphoric acid when a heel from a previous reaction run is used to slurry the metal oxide rather than using water.

In a preferred embodiment of the invention, a high surface area metal oxide (e.g., a surface area of no less than about 4 $m^2$ per gram) is used in the neutralization step resulting in higher metal to phosphorus ratios than are obtained by the use of metal oxides having a surface area lower than 4 $m^2$ per gram. To illustrate this aspect of the invention, the following examples are given utilizing zinc oxide with various surface areas.

TABLE 5

| Run No. | ZnO Surface Area ($m^2$/g) | Zn (wt. %) | P (wt. %) | Zn/P ratio | Visc 40° C. (cSt) | TBN (mg KOH/g) | pH |
|---|---|---|---|---|---|---|---|
| 1 | 7 to 9 | 9.43 | 7.73 | 1.22 | 301 | 15.6 | 6.4 |
| 2 | 5 to 7 | 9.20 | 7.80 | 1.18 | 274 | 6.1 | 6.4 |
| 3 | 9 | 9.55 | 7.74 | 1.23 | 327 | 10.9Π | 6.5 |

TABLE 5-continued

| Run No. | ZnO Surface Area (m²/g) | Zn (wt. %) | P (wt. %) | Zn/P ratio | Visc 40° C. (cSt) | TBN (mg KOH/g) | pH |
| --- | --- | --- | --- | --- | --- | --- | --- |
| 4 | 3.1 | 9.11 | 7.79 | 1.17 | 286 | 5.8 | 6.2 |
| 5 | 7.5 | 9.66 | 7.81 | 1.24 | 382 | 15.9 | 6.3 |
| 6 | 0.5 | 8.88 | 7.84 | 1.13 | 247 | 3.5 | 5.8 |
| 7 | 9.0 | 9.33 | 7.75 | 1.20 | 290 | 10.1 | 7.1 |
| 8 | 3 to 5 | 8.97 | 7.79 | 1.15 | 285 | 5.2 | 6.1 |
| 9 | 3 to 5 | 9.62 | 7.86 | 1.22 | 768 | 13.3 | 6.5 |
| 10 | 4 to 6 | 9.36 | 7.87 | 1.19 | 338 | 7.6 | 6.5 |
| 11 | 5.8 | 9.02 | 7.80 | 1.16 | 294 | 8.0 | 6.4 |
| 12 | 3.5 | 9.03 | 7.85 | 1.15 | 285 | 4.1 | 6.4 |

In the next series of runs, the use of high surface area metal oxides combined with the procedures of Examples 2 and 3 is illustrated. Runs 13 and 15 utilize the standard procedure of Example 2. In runs 14 and 16, the heel procedure of Example 3 was used wherein the heel was 20 wt. % of the amount of thioacid and zinc oxide charged to the reactor and ⅔ of the water was charged to the reaction mixture 10 minutes after the thioacid addition was complete.

TABLE 6

| Run No. | ZnO Surface Area (m²/g) | Zn (wt. %) | P (wt. %) | Zn/P ratio | Visc 40° C. (cSt) | TBN (mg KOH/g) | pH |
| --- | --- | --- | --- | --- | --- | --- | --- |
| 13 | 5 to 7 | 9.52 | 7.91 | 1.20 | 339 | 9.6 | 6.6 |
| 14 | 5 to 7 | 10.06 | 8.20 | 1.23 | 379 | 14.4 | 6.6 |
| 15 | 7 to 9 | 9.52 | 7.89 | 1.21 | 337 | 12.6 | 6.5 |
| 16 | 7 to 9 | 9.85 | 7.77 | 1.27 | 417 | 18.7 | 6.7 |

In all of the above runs, the zinc and phosphorus were determined utilizing the following techniques.

Phosphorus Determination in Metal Salt Product

Equipment:
1. Hitachi U-1100 Spectrophotometer
2. Tall form digestion beakers, 300 mL (Available from Curtin Matheson Scientific, Cat. #030–114)

Reagents:
1. Sulfuric acid solution (1:1 on a volume basis)
2. Nitric Acid (concentrated)
3. Perchloric Acid (70 wt. %)
4. Ammonia meta vanadate solution (25 wt. %, $NH_4VO_3$)
5. Ammonium molybdate tetrahydrate solution (5 wt. %, $(NH_4)_6MO_7O_{24}$)

Procedure

Weigh 0.4 to 0.6 grams of metal salt of di-hydrocarbyl dithiophosphoric acid into a clean, dry 300 mL tall form beaker. To the beaker, add the following reagents in the order listed, down the side of the beaker:
  10 mL of sulfuric acid (1:1),
  10 mL of concentrated nitric acid, and
  7 mL of 70 wt. % perchloric acid.
Cover the beaker with a 10 cm watch glass and set the beaker on a hot plate set on medium under a hood. After initial charring, set the hot plate on high. After digestion of the organic material is complete, remove the beaker from the hot plate and allow the sample to cool to room temperature under a hood for 10 to 15 minutes. Transfer the digested solution to a 250 to 500 mL volumetric flask and dilute to the volume of the flask using distilled water. Stopper the flask and mix the water and digested solution thoroughly. Transfer 15 to 20 mL of the water and digested solution mixture to a 100 mL volumetric flask and add 10 mL of 1:2 nitric acid solution, 10 mL of 0.25 wt. % ammonium meta vanadate solution, and 10 mL of 5 wt. % ammonium molybdate solution to the flask. Dilute the flask to the volume of the flask using distilled water, mix thoroughly and allow the mixture to stand for 20 minutes. Set the spectrophotometer to 465 nm with the UV lamp off and the VIS lamp on and set the sipping time to 5 and run the sample. The wt. % phosphorus is determined by the following calculation:

$$P(\text{wt. }\%) = \frac{B \times A}{10 \times C \times D}$$

wherein P is phosphorus; B is the spectrophotometer reading in ppm P; A is size of volumetric flask in mL (250 or 500 mL flask); C is the amount of water and digested solution mixture in mL (15 or 20 mL); and D is the weight in grams of metal salt of dihydrocarbyl dithiophosphoric acid to be tested.

Zinc Determination in Metal Salt Product

Weigh 1 gram of metal salt of dihydrocarbyl dithiophosphoric acid into a 250 mL Erlenmeyer flask. To the sample, add 100 mL of dioxane and dissolve the sample. Next add 50 mL of 0.1N ethylenediamine tetraacetic acid disodium salt (EDTA) solution into the flask. Place the flask on a low-temperature hot plate under a hood for 10 minutes. The solution should not be heated to a temperature above 80° C. After heating for 10 minutes, remove the flask from the hot plate and add 15 mL of zinc buffer solution (1000 mL of ammonium hydroxide in 600 mL of distilled water to which 200 mL of hydrochloric acid is slowly added). Next, add a stirring bar and place the flask on a lighted stirring plate. While stirring the solution, add 3 to 4 drops of Eriochrome Black T indication solution (1 gram of Eriochrome Black T in 100 mL of dethanolamine, Eriochrome Black T is available from CMS, 11526 Adie Road, Maryland Heights, Mo.). Titrate the solution with 0.1224N standard zinc solution to the Eriochrome Black T endpoint (color change from royal blue to purple). The amount of zinc in the product is determined by the following calculation:

$$Zn(wt. \%) = \frac{((E \times F) - (G \times 0.1224)) \times 3.269}{W}$$

wherein Zn is zinc; E is mL of 0.1N EDTA solution, F is normality of the 0.1N EDTA solution; G is the mL of 0.1224N standard zinc solution; and W is the weight in grams of the product sample.

The foregoing hydrocarbyl dithiophosphoric acid compounds may be neutralized by the process of this invention either alone or in combination with one or more carboxylic acid reactants to obtained a mixed phosphorus-acid salt and carboxylic acid salt. Suitable carboxylic acid reactants include the mono- and polycarboxylic acids containing from about 2 to about 40 carbon atoms, and preferably from about 2 to about 20 carbon atoms. The preferred carboxylic acids are those having the formula RCOOH, wherein R is an aliphatic or alicyclic hydrocarbon-based group preferably free from acetylenic unsaturation. Suitable acids include acetic, propionic, butanoic, hexanoic, decanoic, dodecanoic, octadecanoic, and eicosanoic acids, as well as olefinic acids such as acrylic, oleic, linoleic, and linoleic acid dimer. Typically, R is a saturated aliphatic radical and especially a branched alkyl radical such as the isopropyl or 3-heptyl radical.

When used, the carboxylic acid reactant will be present in an amount such that the metal salt formed from the neutralization of a mixture of (a) hydrocarbyl dithiophosphoric acid and (b) carboxylic acid will be in a weight ratio within the range of from about 0.5:1 to about 500:1 component (a) salt to component (b) salt. Suitable ratios range from about 2.5:1 to about 4.25:1 based on the weight ratio of the salts of component (a) to component (b). Alternatively, each of components (a) and (b) may be neutralized in separate reaction vessels by the process of this invention and then the resulting salts can be combined to give a product contains salts of (a) and (b) within the desired ratios.

Accordingly, the invention is subject to considerable variation within the spirit and scope of the appended claims.

What is claimed is:

1. A process for preparing an overbased metal salt of hydrocarbyl dithiophosphoric acid comprising:
    a) forming a reaction mixture containing (i) basic metal salt of hydrocarbyl dithiophosphoric acid, and (ii) metal oxide wherein the weight ratio of (i) to (ii) is within the range of from about 0.5:1 to about 4:1 which metal oxide has a surface area of no less than about 4 $m^2$ per gram up to about 12 $m^2$ per gram;
    b) feeding to the reaction mixture in (a) hydrocarbyl dithiophosphoric acid thereby forming a reaction mass;
    c) subsequent to step (b) feeding from about 1 to about 8 moles of water per mole of metal oxide to the reaction mass; and
    d) reacting the reaction mass in (c) at a temperature and for a period of time, which time and temperature are sufficient to form basic metal salt of dihydrocarbyl dithiophosphoric acid having a base metal to phosphorus weight ratio within the range of greater than about 1.2:1 up to about 1.3:1.

2. The process of claim 1 wherein the hydrocarbyl dithiophosphoric acid is the reaction product of phosphorus sulfide and aliphatic alcohol containing from 3 to 40 carbon atoms.

3. The process of claim 1 wherein the metal oxide is zinc oxide.

4. The process of claim 3 wherein the zinc oxide has a surface area of no less than about 5 $m^2$ per gram up to about 10 $m^2$ per gram.

5. The process of claim 2 wherein the metal oxide is zinc oxide.

6. The process of claim 5 wherein the zinc oxide has a surface area of no less than about 5 $m^2$ per gram up to about 12 $m^2$ per gram.

7. The process of claim 6 wherein the aliphatic alcohol is 2-ethylhexanol.

8. The process of claim 1 wherein the overbased metal salt of hydrocarbyl dithiophosphoric acid is predominantly di-2-ethylhexyl-dithiophosphate having a zinc to phosphorus weight ratio within the range of greater than about 1.2:1 up to about 1.3:1.

9. The process of claim 2 wherein the aliphatic alcohol is 2-ethylhexanol.

10. The process of claim 1 wherein the weight ratio of (i) to (ii) is within the range of from about 1:1 to about 2:1.

11. The process of claim 7 wherein the weight ratio of (i) to (ii) is within the range of from about 1:1 to about 2:1.

12. The process of claim 11 wherein from about 2.5 to about 7 moles of water per mole of metal oxide is fed to the reaction mass in step (c).

13. The process of claim 1 wherein the reaction mixture of step (a) further contains a catalytic amount of sodium hydroxide.

14. The process of claim 1 wherein the reaction mixture of step (a) further contains a catalytic amount of potassium hydroxide.

15. The process of claim 1 further comprising feeding an amount of aliphatic monocarboxylic acid containing from 2 to 20 carbon atoms to the reaction mixture of step (b), which amount is sufficient to form a mixed salt containing (I) basic metal salt of hydrocarbyl dithiophosphoric acid and (II) basic metal salt of carboxylic acid having a weight ratio within the range of about 2.5:1 to about 4.25:1 salt of (I) to salt of (II).

* * * * *